(12) United States Patent
Hashimoto et al.

(10) Patent No.: US 9,833,340 B2
(45) Date of Patent: Dec. 5, 2017

(54) DETECTION DEVICE OF LOAD AND MOMENT, AND ARTIFICIAL LIMB INCLUDING THE DETECTION DEVICE

(75) Inventors: Hiroaki Hashimoto, Kobe (JP); Takuya Shirata, Tokyo (JP)

(73) Assignee: NABTESCO CORPORATION, Tokyo (JP)

( * ) Notice: Subject to any disclaimer, the term of this patent is extended or adjusted under 35 U.S.C. 154(b) by 0 days.

(21) Appl. No.: 14/424,208

(22) PCT Filed: Aug. 30, 2012

(86) PCT No.: PCT/JP2012/072030
§ 371 (c)(1),
(2), (4) Date: May 18, 2015

(87) PCT Pub. No.: WO2014/033877
PCT Pub. Date: Mar. 6, 2014

(65) Prior Publication Data
US 2015/0297366 A1 Oct. 22, 2015

(51) Int. Cl.
*A61F 2/70* (2006.01)
*A61F 2/76* (2006.01)
(Continued)

(52) U.S. Cl.
CPC .................. *A61F 2/70* (2013.01); *A61F 2/76* (2013.01); *G01L 1/2206* (2013.01);
(Continued)

(58) Field of Classification Search
CPC ...... A61F 2/70; A61F 2/76; A61F 2002/7635; A61F 2002/7645; G01L 1/22
See application file for complete search history.

(56) References Cited

U.S. PATENT DOCUMENTS

2004/0045372 A1  3/2004  Liu et al.
2008/0139970 A1*  6/2008  Macomber ............... A61F 2/60
                                                              600/595
(Continued)

FOREIGN PATENT DOCUMENTS

CN       1074109 A     7/1993
JP       S49-7033 B1   2/1974
(Continued)

OTHER PUBLICATIONS

First Notification of Reason for Rejection as issued in Chinese Patent Application No. 201280075538.8, dated Oct. 14, 2015.
(Continued)

*Primary Examiner* — Bruce E Snow
*Assistant Examiner* — Melissa Hoban
(74) *Attorney, Agent, or Firm* — Pillsbury Winthrop Shaw Pittman, LLP (57) ABSTRACT

The present invention provides a detection device for detecting a load and moment and capable of increasing the output by a strain gage. The detection device is provided with a characteristic sensor block. The sensor block includes a base having an axis extending in the direction of a load to be detected, a front side wall raised from the base at a position offset from the axis of the base, a rear side wall raised from the base at a position offset from the axis of the base in the direction opposite the front side wall, and an upper wall for connecting the upper end of the front side wall and the upper end of the rear side wall. The sensor block supports each strain gauge on the upper surface of the upper wall. The upper wall includes a center portion located at the center between the front side wall and the rear side wall, a first portion located between the center portion and the front side wall, and a second portion located between the center portion and the rear side wall. The first portion and the
(Continued)

second portion, which support the strain gauges, have a smaller thickness than the center portion and are relatively easily deformed or strained.

13 Claims, 8 Drawing Sheets

(51) Int. Cl.
*G01L 1/22* (2006.01)
*G01L 5/16* (2006.01)
*G01L 5/22* (2006.01)
*A61F 2/64* (2006.01)

(52) U.S. Cl.
CPC ............ *G01L 1/2287* (2013.01); *G01L 5/161* (2013.01); *G01L 5/226* (2013.01); *A61F 2/644* (2013.01); *A61F 2002/704* (2013.01); *A61F 2002/7635* (2013.01); *A61F 2002/7645* (2013.01)

(56) References Cited

U.S. PATENT DOCUMENTS

| 2008/0276725 | A1 | 11/2008 | Pusch |
| 2011/0197682 | A1* | 8/2011 | Palmer .................... A61F 2/76 |
| | | | 73/862.045 |

FOREIGN PATENT DOCUMENTS

| JP | 63-210633 | A | 9/1988 |
| JP | 63-286731 | A | 11/1988 |
| JP | 2003-070817 | A | 3/2003 |
| JP | 2009-513955 | A | 4/2009 |
| JP | 2010-008343 | A | 1/2010 |
| KR | 10-2011-0098070 | A | 9/2011 |
| WO | WO 01/72245 | A | 10/2001 |
| WO | WO 2007/048374 | A1 | 5/2007 |
| WO | WO 2011/100117 | A2 | 8/2011 |
| WO | WO 2012/033018 | A1 | 3/2012 |

OTHER PUBLICATIONS

International Preliminary Report on Patentability and the Written Opinion of the International Searching Authority as issued in International Application No. PCT/JP2012/072030, dated Mar. 3, 2015 (Forms PCT/IB/373 & PCT/ISA/237).
International Search Report as issued in International Patent Application No. PCT/JP2012/072030, dated Oct. 30, 2012.
Extended European Search Report as issued in European Patent Application No. 12883683.0, dated May 4, 2016.

* cited by examiner

DETECTION DEVICE OF LOAD AND MOMENT, AND ARTIFICIAL LIMB INCLUDING THE DETECTION DEVICE

CROSS-REFERENCE TO RELATED APPLICATION

This application is the U.S. National Stage of PCT/JP2012/072030, filed Aug. 30, 2012. The content of this application is incorporated herein by reference in its entirety.

TECHNICAL FIELD

This invention relates to a detection device for detecting a load and moment comprising a sensor block subject to an external force and a strain gauge supported by the sensor block and adapted to detect a load and moment which is a component or an ingredient of the external force, and particularly to a technique which is effective for obtaining a large strain output. Also, this invention relates to an artificial limb (this limb includes a hand and a leg of a robot) such as an artificial leg or an artificial arm incorporated with the afore-mentioned detection device.

BACKGROUND ART

In this kind of artificial limb, it is necessary to know correctly in what state or phase it is, because the correct knowledge ensures an appropriate controlling operation. Reviewing an artificial leg, for example, it is important to know in what phase the artificial leg is, i.e., whether it is in a swing phase or stance phase, or whether it is in a level walking or hill walking. The load and moment, as well as a knee angle, which are taken as an agenda in this invention, are important factors to find out such phases. Although an artificial leg will be described hereinafter as an object to which the present invention is applied, the present invention is, as a matter of course, likewise applicable to any artificial limb.

A first method for measuring or detecting a load (or force in an axial direction) and moment is to detect the load and the moment independently. Patent Documents 1 and 2 show such a first method. A second method is to obtain a mixed information of the load and moment all together, then separate such obtained mixed information by calculation and obtain each information of the load and the moment. Patent Document 3 shows the second method. The first and second methods are based on such an assumption that a detection device including a sensor block and a strain gauge is built in an artificial limb and the detection device itself is used as one component part of the artificial limb as generally practiced.

Separately from the technique in which the detection device is used as a component part of the artificial limb, another technique is also known in which a detection device is temporarily built in an artificial limb, then analysis and evaluation (evaluation whether it is well fit to the wearer) with respect to the artificial limb are performed, and thereafter, the detection device is replaced with a predetermined component part (for example, rotary adapter) of the artificial limb. Patent Document 4 shows the technique in which a detection device is temporarily built in an artificial limb.

PRIOR ART PATENT DOCUMENTS

Patent Document 1: WO 2011/100117
Patent Document 2: Official Gazette of Japanese Patent Application Laid-Open No. 2003-70817
Patent Document 3: WO 2001/072245
Patent Document 4: WO 2007/048374 (corresponding to Official Gazette of Japanese Translation of PCT International Application Publication No. 2009-513198)

SUMMARY OF INVENTION

Problem to be Solved by Invention

In the first method in which the information of a load and a moment is detected independently, the sensor block requires two planes perpendicular to each other in order to support the strain sensor. In order to fulfill this requirement, the sensor block includes, as shown for example in Patent Documents 1 and 2, an hollow interior structure having a ring-like configuration in section and the strain gauge is required to be disposed at an internal plane of the hollow interior structure. In this respect, it is required for the first method to have a number of double of strain gauges because the information of the load and moment is not commonly used. Therefore, it gives rise to such an inconvenience that the operation for providing such many strain gauges is troublesome and much time and labor are required for making the detection device.

The second method has such an advantage that the number of strain gauges required is relatively small. Notwithstanding the first and second methods, however, the strain gauge should be designed such that a large output can be provided in order to carry out a signal processing effectively. To this end, it is desired that the sensor block portion, which supports the strain gauges, produces a greater strain. However, in order to obtain a greater strain, the sensor block tends to become large in size, and thus becomes an obstacle to downsize the detection device.

For example, reviewing Patent Document 4 from the viewpoint of obtaining a large strain amount, a supporting post is provided at each corner of a square flange and each strain gauge is disposed at a position slightly away from the supporting post (i.e., fixing portion) on the flange. Since there is some distance from the fixing portion to the position where the strain gauge is disposed, the external force is applied to each strain gauge as a bending force. However, the above-mentioned some distance is small, the amount of strain is small and the output of the strain gauge is low.

It is, therefore, an object of the present invention to provide a detection device capable of increasing the bending by an external force while downsizing a sensor block, and capable of increasing an output by a strain gauge.

Another object of the invention is to provide a detection device wherein an amplifier for amplifying a detection output of a strain gauge can be disposed at a position very close to the strain gauge. Other objects of the present invention will become more manifest from the description to follow.

Means for Solving the Problem

In the present invention, the second method is employed in which the number of the required strain gauges is small. And a sensor block for supporting each strain gauge is provided with a specific construction in order to increase the output of each strain gauge. That is, the sensor block includes a base having an axis extending in a direction of a load to be detected, a front side wall raised from the base at a position offset from the axis of the base, a rear side wall raised from the base at a position offset from the axis of the base in the direction opposite the front side wall, and an upper wall for connecting an upper end of the front side wall and an upper end of the rear side wall.

The sensor block has an integral structure as a whole. As for material of the sensor block, it is required to have such characteristics as excellent in corrosion resistance and in mechanical strength, Young's modulus being small, plastic deformation being difficult to occur (or stress resistance is large) and thermal expansion being difficult to occur. From the viewpoint of light-weight of an artificial limb, the weight of the sensor block is also very important. When such wide varieties of characteristics are taken into consideration, material suitable for the sensor block is, for example, metal such as aluminum or aluminum alloy, stainless steel and titanium or titanium alloy, or alloy such metal.

The sensor block supports the strain gauges at an upper surface of the upper wall. The portion of the upper wall where the strain gauges are disposed is designed so as to be more susceptible to deform under the effect of external force than the rest portion of the upper wall. The upper wall will now be described in more detail. The upper wall includes a center portion located at a center between the front side wall and the rear side wall, a first portion located between the center portion and the front side wall and a second portion located between the center portion and the rear side wall. The center portion is a portion which is perpendicular to the offset direction of the front and rear side walls. The first and second portions, which support the strain gauges, are located at both sides of the center portion.

The center portion has, for example, a larger thickness than the first and second portions and thus, it has a large rigidity, thereby hardly deformed. The center portion may be provided with a rib in order to increase rigidity. Contrary to such a center portion as just mentioned, the first and second portions supporting the strain gauges, are, for example, small in thickness and relatively susceptible to deform or strain. The strain gauges consist of two kinds or two groups of gauges, the first strain gauges being located on the upper surface of the first portion of the upper wall and the second strain gauges being located on the upper surface of the second portion of the upper wall.

Generally used as the first and second strain gauges are resistance wire strain gauges. In the alternative, semiconductor strain gauges of higher output may also be used. Since those strain gauges are provided to the upper surface of the upper wall of the sensor block, the bonding operation thereof is easy. The first and second strain gauges are symmetrically arranged with respect to the center portion of the upper wall. Owing to the foregoing arrangement, the first and second strain gauges are in a mutually complementary relationship and thus preferable in respect of temperature characteristics. In addition, the first and second strain gauges having a symmetrical arrangement exhibit such an advantage that the calibration can effectively performed in consideration of the bonding errors.

A mixed information of a load in one direction and a moment on one plane is detected by such first and second strain gauges. The load in one direction is a load in a direction extending along the axis of the base of the sensor block, and the moment on one plane is a moment extending in each offset direction of the front and rear side walls and on a place perpendicular to the upper surface of the upper wall.

In the present invention, the attachment parts of an object (for example, artificial leg) adapted to detect the load and moment and of the sensor block are located respectively on opposite ends of the center portion of the sensor block in a direction perpendicular to the offset direction of the front and rear side walls. Through the opposite end parts of the center portion, the object adapted to detect the load and moment is attached or fixed.

As means for fixing the opposite end parts of the center portion, a general method using a plurality of fixing screws can be employed. However, it is preferable to use a ring-like fixing screw member. The reason is that in doing so, the amplifier for amplifying the detection output of the strain gauge can be arranged in the inner circumferential space which is defined by the ring-like fixing screw member. Moreover, since the fixing screw member surrounding the amplifier is a conductor, there can be expected the shielding effect against radiation waves. Owing to the fixture by using such fixing means, the center portion of the upper wall of the sensor block can be firmly fixed as if the whole center portion were fixed in spite of the fact that the center portion is fixed only at both end parts thereof. The reason is that the center portion is a rigid body which is high in rigidity and difficult to be deformed.

The sensor block is provided with a space defined by the base, the upper wall, the front side wall and the rear side wall. Owing to this arrangement, the external force applied to the base is transmitted to the upper wall through the front and rear side walls. The upper wall portion to which the external force is applied and the fixing portion located at the center portion of the upper wall are away from each other by a distance equal to a half of the diameter of the upper wall. Owing to this feature, the external force transmitted to the upper wall through the front and rear side walls renders a relatively large bending to the first and second portions of the upper wall. Since the bending is large, the strain caused by the bending is large and the strain outputs of the first and second strain gauges for detecting the strain become also large.

In order to obtain sufficient durability and enable prolonged use, it is preferable to restrict the range of bending of the upper wall. As means for restricting or limiting the bending, there can be employed stopper means which includes a first stopper for defining the limit of the bending in one direction and a second stopper for defining the limit of the bending in the opposite direction. The first and second stoppers may be provided at outer peripheral portions of the front and rear side walls, respectively. The stoppers can also be provided at the artificial leg side. However, it is preferable to provide the stoppers at the sensor block side for the purpose of management of tolerance.

The detection device of the present invention may be integrally built in the artificial limb so that the detection device can be used as one of the component elements of the artificial limb. In the alternative, it is also acceptable that the detection device is temporarily built in the artificial limb so that it can be used for evaluation or adjustment as for the use of the artificial limb. Especially, in the case where the detection device is integrally built in the artificial limb, it is preferable that the sensor block of the detection device is used as an alignment block of the artificial limb.

The first and second strain gauges detect the mixed information including a load and moment. Those strain gauges are symmetrically arranged with respect to the fixing part of the center portion. Owing to the foregoing arrangement, in the first and second strain gauges, the loads of the same magnitude act in the same direction and the moments of the same magnitude act mutually in the opposite directions. Therefore, the load information can be obtained by adding the output signals coming from the respective strain gauges, and the moment information can be obtained by subtraction processing. Such arithmetic processing as just mentioned can be performed by a control microcomputer provided to an artificial limb itself such as an artificial leg, or by a specific operational amplifier.

BEST MODE FOR CARRYING OUT THE INVENTION

Figure 1:
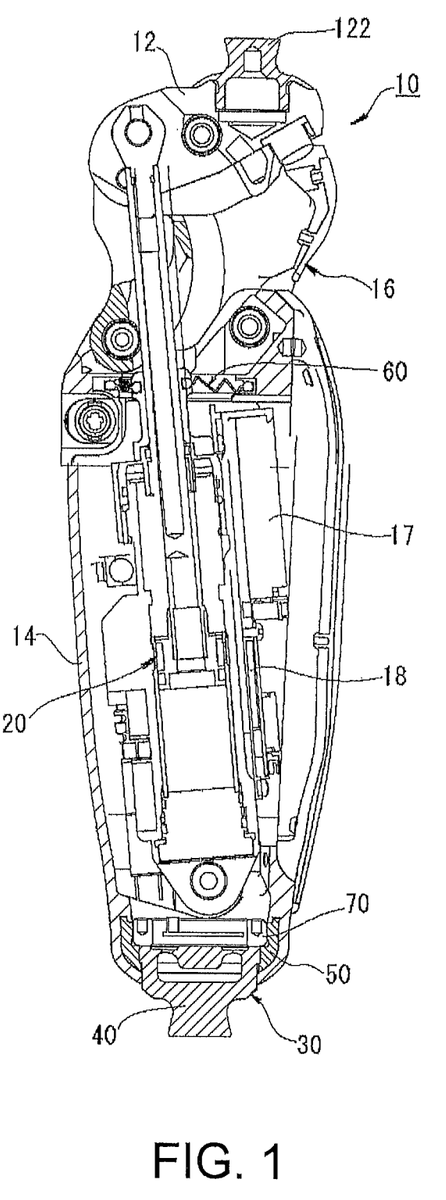
FIG. 1 is a sectional structural view showing one embodiment of an artificial leg with a detection device of the present invention built therein.

FIG. 1 shows one embodiment of the present invention which is a multi-axis artificial leg with a detection device built therein, and particularly, it mainly shows a knee coupling portion. An artificial leg 10, that is a thigh artificial leg, comprises an upper member 12 located at an upper side of the knee, and a lower member 14 located at a lower side of the knee and bendably or swingably connected to the upper member 12 so as to enable the knee to bend. The upper member 12 is in a plate form including two plate portions, while the lower member 14 is in a frame form defining an internal space.

An upper end part of the upper member 12 is to be attached with a socket (not shown) for constituting the thigh, while a lower end part of the lower member 14 is to be attached with a leg member (not shown) for constituting the leg part. At that time, in order to properly determine the position of the axis, each attachment part is provided with an alignment block. In the artificial leg 10 here, the upper member 12 side is provided with a normal alignment block 122, while the lower member 14 side is provided with a sensor block 40, that is a component part of a detection device 30. The sensor block 40 exhibits a function as an alignment block. Of course, the detection device may also take such a form that an artificial leg and a leg part are simply jointed with each other irrespective of the alignment (for example, the sensor block does not include a pyramid part).

The detection device 30 includes a metal-made sensor bracket 50 as a connection member for connecting the sensor block 40 to a carbon frame that is the lower member 14. The sensor bracket 50 is integrally formed with a carbon frame that is the lower member 14 and located at a lower inner periphery of the lower member 14. Accordingly, the detection device 30 for detecting a load and moment is integrally united with the component parts of the artificial leg 10.

In addition to the detection device 30, the artificial leg 10 also includes a bellows packing means 60 for waterproofing and dustproofing. The rest of its structure is about the same as a general artificial leg. For example, the upper member 12 and the lower member 14 are connected to each through a knee coupling 16. The knee coupling 16 is comprised of a four-node link mechanism. The frame 14, that is a lower member, is provided at an inner side thereof with a battery 17 and a control circuit 18 for the use of electronic control. The frame 14 is further provided at the inner side thereof with a hydraulic cylinder 20 for assisting or limiting the movement of the knee coupling 16. It is well known that the hydraulic cylinder 20 limits the movement of the knee coupling 16 in accordance with the flow resistance of the hydraulic fluid passing through the restriction.

Figure 2:
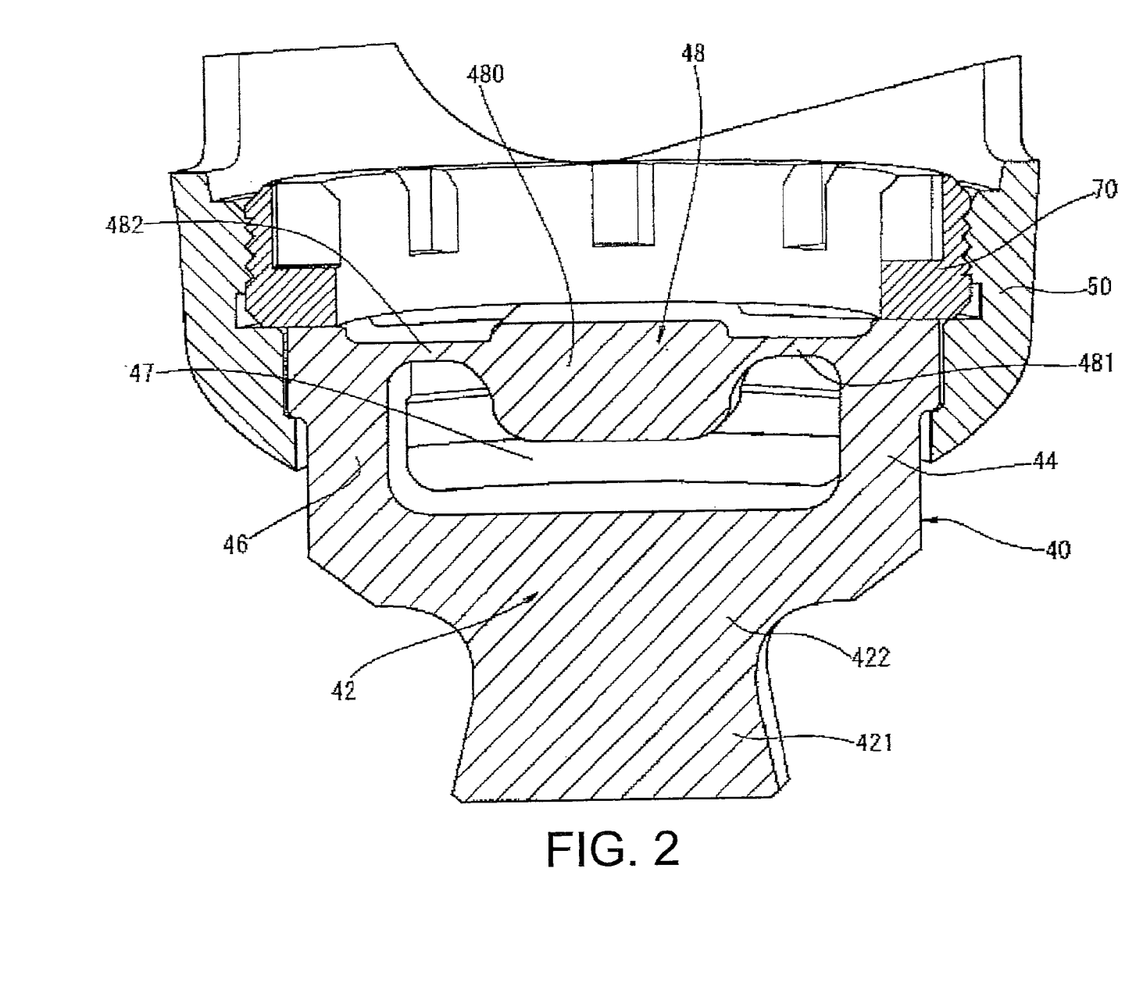
FIG. 2 is a sectional view showing a built-in state of the detection device of FIG. 1.
Figure 3:
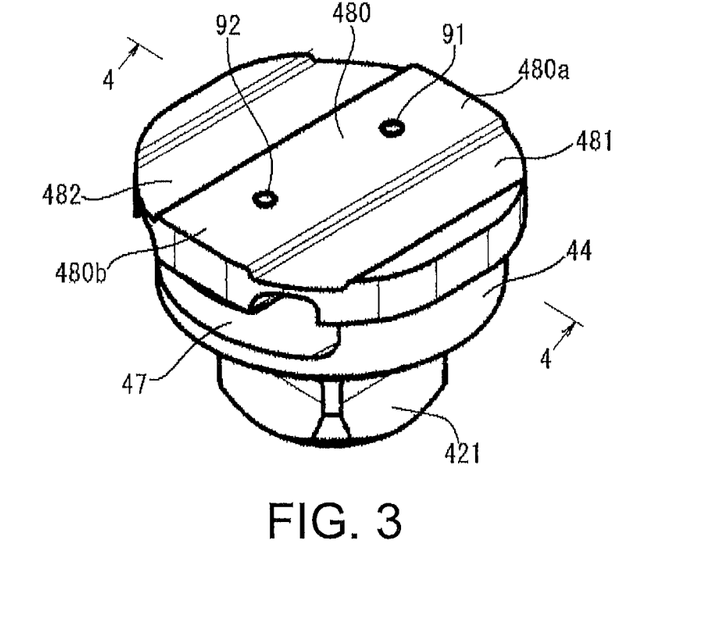
FIG. 3 is a perspective view showing a sensor block which is employed in the detection device.
Figure 4:
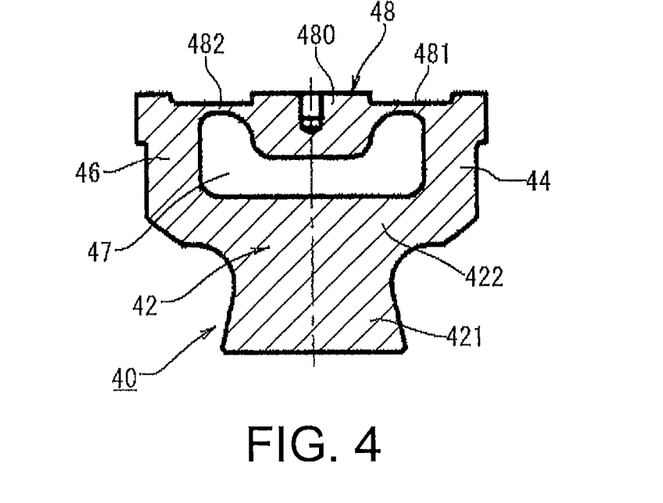
FIG. 4 is a sectional view taken on line 4-4 of FIG. 3.

The structural characteristics of the detection device 30 will now be described with reference to FIGS. 2 through 4. An important structural part of the detection device 30 is, for example, a sensor block 40 made of titanium. The sensor block 40 is an integral metal workpiece and comprises a base 46 including a pyramid part 421; a front side wall 44 and a rear side wall 46 raised from the base 42; and an upper wall 48 disposed between the front and rear side walls 44, 46.

In addition to the pyramid part 421, the base 42 comprises a base body 422 having a larger diameter than the pyramid part 421. The outer diameter of the base body 422 is, for example, about 30 to 35 mm. The axis of the base 42, which is in alignment with that of the pyramid part 421, extends in the direction of the load to be detected.

The sensor block 40 is a plane symmetry, and its symmetric plane is a specific plane including the axis of the base 42. The base 42, more specifically, the two side walls 44, 46 raised from the base body 422 having a large diameter are offset in the mutually opposite directions from the specific plane including the axis, and the front and rear side walls 44, 46 spaced away from each other have a mutually symmetrical three-dimensional configuration. The terms "front" and "rear" used here with respect to the side walls correspond to the walking directions of the artificial leg 10. Specifically, the "front" refers to the front side of the walking direction, while the "rear" refers to the rear side of the walking direction. Therefore, in the artificial leg 10, the front side wall 44 refers to a side wall located at the front side of the walking direction, while the rear side wall 46 refers to a side wall located at the rear side of the walking direction.

From the viewpoint of the "front" and "rear", the upper wall 48 extends in a direction connecting the "front" and the "rear". In other words, the upper wall 48 extends in the walking direction. The upper wall 48 connects the upper end of the front side wall 44 and the upper end of the rear side wall 46 and defines a space 47 between the upper wall 48 and the upper surface of the base body 422 of the base 42. The shape and the width of this space 47 affect the output of the detection device 30. If the width is too small, the output will become small. However, if the width is too large, mechanical breakage is liable to occur. Especially, the affection onto the output depends on the width of the portions where the strain gauges are arranged, i.e., the width of the first and second portions 481, 482. Therefore, the shape and the size of the space 47 are determined while taking the foregoing into consideration. The width of the space 47 itself is, for example, about 25 mm.

The upper wall 48 is thick at the center part 480 located at the center between the front side wall 44 and the rear side wall 46, and thin at the first and second parts 481, 482 on both sides adjacent to the center portion. The center portion 480 is a part including the attachment parts connected to the lower member 14 of the artificial leg 10. The attachment parts 480a, 480b are located at lengthwise both ends of the center portion 480. Those attachment parts 480a, 480b are portions for attaching the sensor block 40. In order to achieve a stable fixing, the attachment parts 480a, 480b are large in thickness at the center portion 480 and perform like a rigid body as a whole.

The sensor block 40 is fit to the inner periphery of the sensor bracket 50 which is integral with the lower member 14 and fixed by a sensor fixing screw 70. The sensor fixing screw 70 has a ring-like configuration. By being screwed, the lower surface of the sensor fixing screw 70 presses the attachment parts 480a, 480b at the both ends of the center portion 480 from the above and fixed. In that case, the center portion 480 of the upper wall 48 is subject to the tightening force or pressing force of the sensor fixing screw 70 from the upper surface side with the lower surfaces of the attachment parts 480a, 480b at the both ends abutted with a step of the sensor bracket 50. Thus, the actual pressing made by the sensor fixing screw 70 is applied only to the both end parts of the center portion 480. However, since the center portion 480 itself has a large rigidity, the same effect is produced as that the censor block 40 is fixed at the center of the upper wall 48. The sensor fixing screw 70 is preferably of the so-called twist lock type but it may take any general screw form. In order to reliably restrain the rotation between the sensor block 40 and the sensor bracket 50 by the fixing operation, it is preferable to provide a rotation prevention means between the outer peripheral portion (specifically, the outer peripheral portion of the upper wall 48) of the sensor block 40 and the inner peripheral portion of the sensor bracket 50. As such rotation prevention means, a stop screw may be employed. Most preferably, however, a circumferential plane and a non-circumferential plane (planar plane and curved plane) are provided at the mutually fitting portion. In FIG. 3, reference numerals 91 and 92 denote attachment screw holes for attaching an amplifier (not shown) for amplifying the detection outputs of the strain gauges, respectively. The amplifier is arranged very close to the inner peripheral space portion of the sensor fixing screw 70 on the upper wall 48, i.e., the strain gauge of the upper surface of the upper wall 48, using the attachment screw holes 91, 92.

In order to carry out the force transmission effectively, the height relations between the upper surface and the lower surface at the center portion 480 of the upper wall 48, and the upper surface and the lower surface at the first and second portions 481, 482 of the upper wall 48 are important. Firstly, the height position of the upper surface of the center portion 480 of the upper wall 48 is higher than the height positions of the upper surfaces of the first and second portions 481 and 482 of the upper wall 48. In the case where those height positions are same, the force escapes from the upper parts of the front and rear side walls 44, 46 and is difficult to be transmitted to the upper wall 48. However, in the present invention, since the height positions are different, the force from the front and rear side walls 44, 46 side can be effectively transmitted to the upper wall 48 side. Secondly, the height position of the lower surface of the center portion 480 of the upper wall 48 is lower than the height positions of the lower surfaces of the first and second portions 481, 482 of the upper wall 48. Owing to the foregoing arrangement, the heights of the lower surfaces of the attachment parts 480a, 480b at the center portion 480 are lower than the height positions of the lower surfaces of the first and second portions 481, 482 of the upper wall 48. Accordingly, there can be prevented the occurrence of such an inconvenience that when the sensor fixing screw 70 is tightened, the force is transmitted to the lower parts of the front and rear side walls 44, 46 and strain occurs onto the first and second portions 481, 482.

The first and second portions 481, 482 having a small thickness are located on the both sides of the center portion 480 having a large thickness at the upper wall 48. Each of the first and second portions 481, 482 is a portion to which the strain gauge is provided. Each of the first and second portions 481, 482 will be eventually subjected to bending-like force in the beam.

Figure 5:
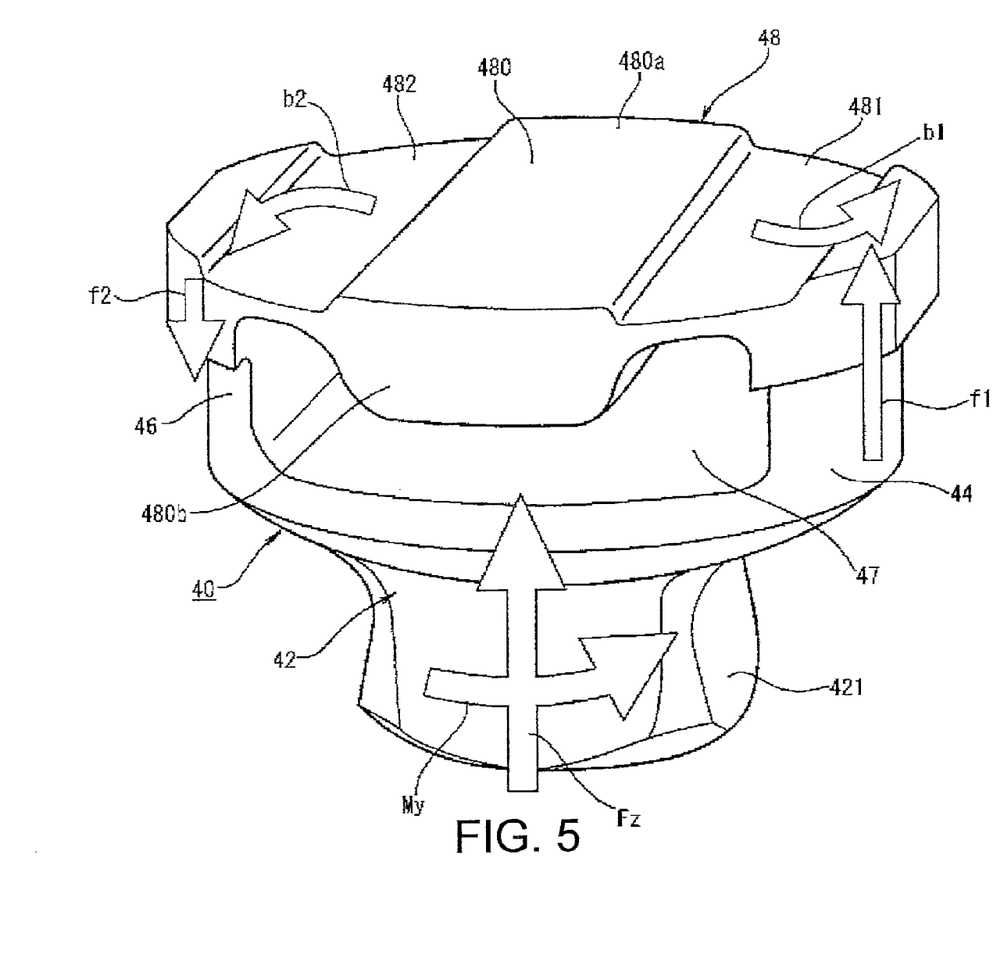
FIG. 5 is an explanatory view showing the transmission of force in the sensor block.

FIG. 5 shows the force transmission in the sensor block 40. As already described, the fixing portion of the sensor block 50 or the attachment parts 480a, 480b are located at the both ends of the center portion 480 of the upper wall 48. The external force is applied through a lower part of the base 42 of the sensor block 40, i.e., through the pyramid part 421. This external force includes a vertical direction Fz extending in a direction of the axis of the base 40 and a moment My on a plane extending in a direction of the running direction of the artificial leg (in other words, the direction connecting the front and rear side walls 44, 45) and perpendicular to the upper surface of the upper wall 48.

The base 42, which includes the pyramid part 421, and the upper wall 48 are separated from each other by the space 47 therebetween. Therefore, the external force applied to the base 42 is transmitted to the upper wall 48 side through the front and rear side walls 44, 46 with the space 47 sandwiched therebetween. For example, a push-up force f1 is applied to the front side wall 44 side, and a pull-down force f2 is applied to the rear side wall 46 side. Since the center portion 480, which is located at an intermediate part between the front and rear side walls 44, 46, is fixed, an upwardly bending force b1 is caused to act on the first portion 481 and a downwardly bending force b2 is caused to act on the second portion 482 by the push-up force f1 and pull-down force f2, respectively. As a result, the strain amounts in the first and second portions 481, 482 are increased compared with the strain amount caused by a simple compression and tensile.

Figure 6:
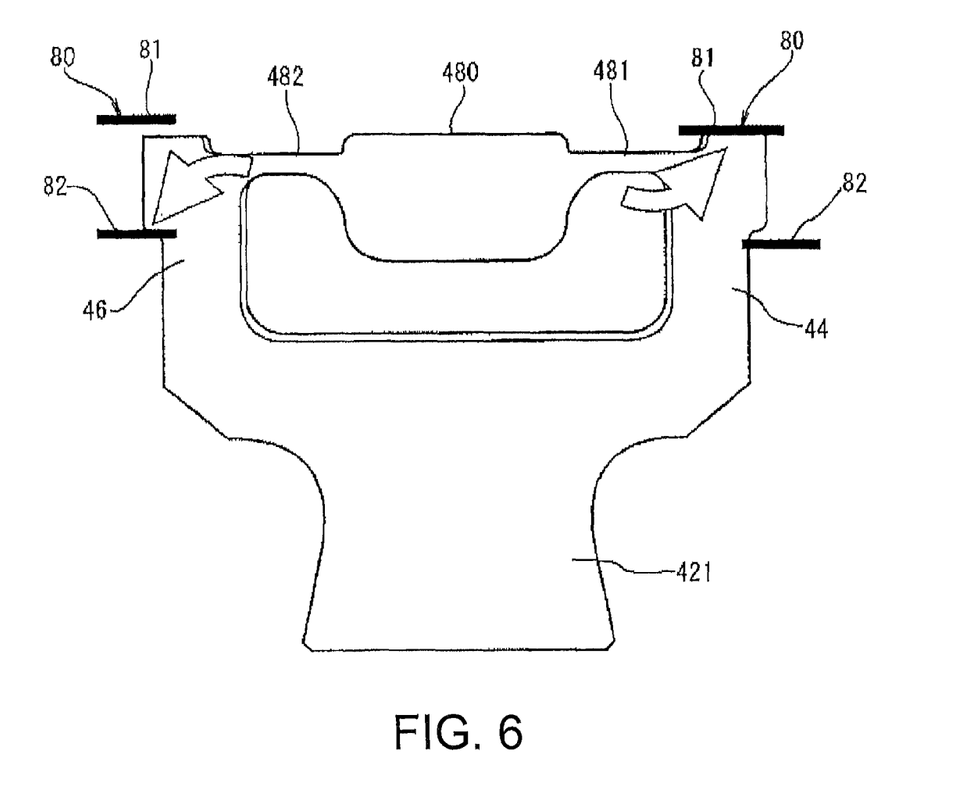
FIG. 6 is an explanatory view showing a stopper means in the detection device.

The phrase "increase of the strain amount" used herein means the increase of the detection sensibility of the detection device 30 and thus, the increase of the strain amount is referable from the viewpoint of increasing the strain output. However, since the first and second portions 481, 482 are susceptible to strain, it cannot be said that there is no possibility of breakage to occur at those portions when a strong load or external force is applied thereto. Therefore, in order to reliably prevent such breakage to occur, it is preferable to restrict the magnitude or range of the bending. As a method for restriction, it is preferable to provide, as shown in FIG. 6, a stopper means 80 for limiting the range of the bending at each portion of the front and rear side walls 44, 46. The stopper means 80 includes a first stopper 81 defining one side of the bending range and a second stopper 82 defining the other side of the bending. Specifically, the bending range can be restricted by abutting the flange of the outer periphery of the upper part of each of the front and rear side walls 44, 46 with the portions of the sensor bracket 50 or the sensor fixing screw 70.

The first bending force f1 converted to the bending brings tensile to a portion 481t closer to the front side wall 44 in the first portion 481 and compression to a portion 481c closer to the center portion 480, respectively. The second bending force F2 brings tensile to a portion 482t closer to the rear side wall 46 in the second portion 482 and compression to a portion 482c closer to the center portion 480, respectively. The acting forces of the compression and tensile are, as a matter of course, oriented in the traveling direction (in other words, the direction connecting the front and rear side walls 44, 46) of the artificial leg. Accordingly, the strain gauges such as the resistance wire strain gauges are bonded in that direction.

Figure 7:
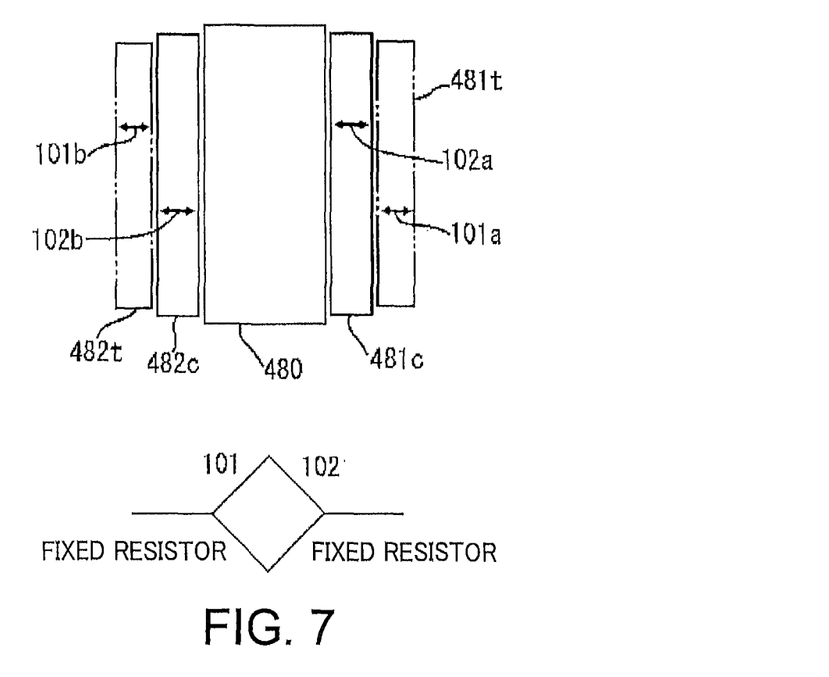
FIG. 7 is a schematic diagram showing a first bonding example of a strain gauge.
Figure 8:
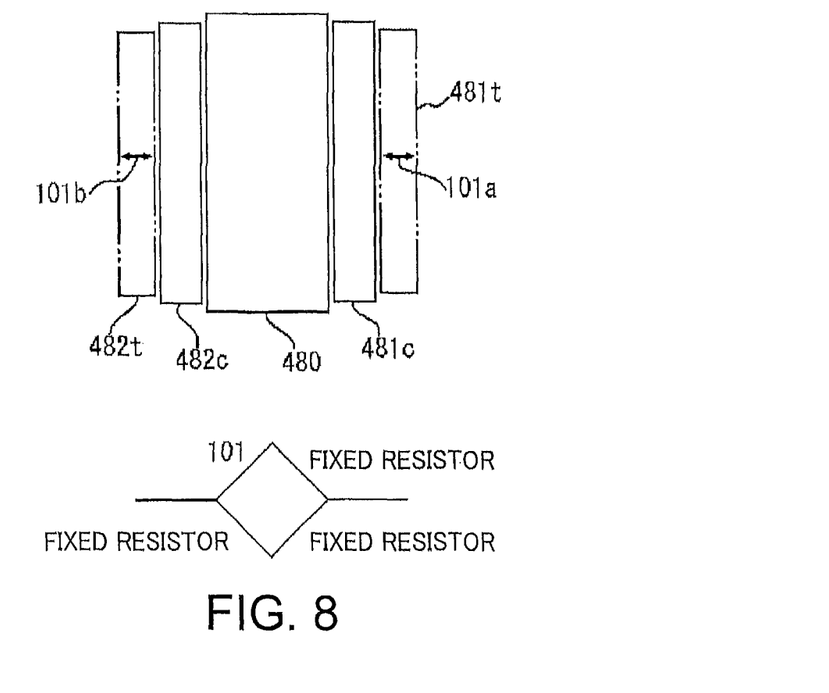
FIG. 8 is a schematic diagram showing a second bonding example of a strain gauge.
Figure 9:
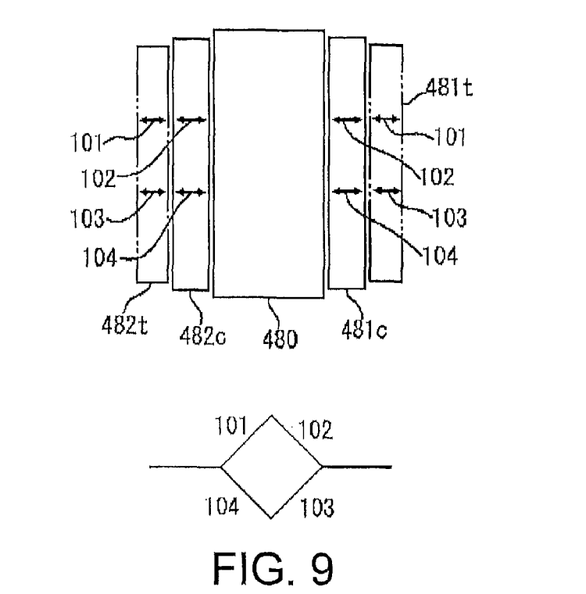
FIG. 9 is a schematic diagram showing a third bonding example of a strain gauge.

FIGS. 7 through 9 show several examples of how to bond the strain gauges. FIG. 7 shows a half bridge having a gauge number 2, FIG. 8 shows a quarter bridge having a gauge number 1, and FIG. 9 shows a full bridge having a gauge number 4. In the half bridge of FIG. 7, the first strain gauge 101a or 101b is bonded to the portions 481t, 482t to which tensile is brought and the second strain gauge 102a or 102b is bonded to the portions 481c, 482c to which compression is brought. In the quarter bridge of FIG. 8, the strain gauge 101a or 101b is bonded to the portions 481t, 482t on the both sides to which tensile is brought. Moreover, in the full bridge of FIG. 9, the strain gauges 101 through 104 are bonded respectively to the portions 481t, 482t on the both sides to which tensile is brought and the portions 481c, 482c on the both sides to which compression is brought.

As shown as an accessory diagram in FIGS. 7 through 9, the strain output is obtained by the general Wheatstone bridge. In that case, it is a matter of course that except, for the full bridge, the four resistors include a fixed resistor. Since the quarter bridge of FIG. 8 has a smaller number of strain gauges, the bonding operation is easier than other bridges, but the others are more advantageous in respect of strain output. The reason is that by taking the difference of the detection outputs of the strain gauges between the respective portions to which tensile and compression are brought, the sensitivity of the strain output can be doubled and the temperature characteristics can be enhanced.

In the present invention, however, since the respective strain gauges are bonded to the upper surface of the upper wall 48 of the sensor block 40 in the respective cases shown in FIGS. 7 through 9, the bonding operation is easy. And the bonding errors of the strain gauges which are to be bonded to the first and second portions 481, 482 at both sides of the center part 480 can be calibrated. Therefore, strict management with respect to the bonding position is not required.

Figure 10:
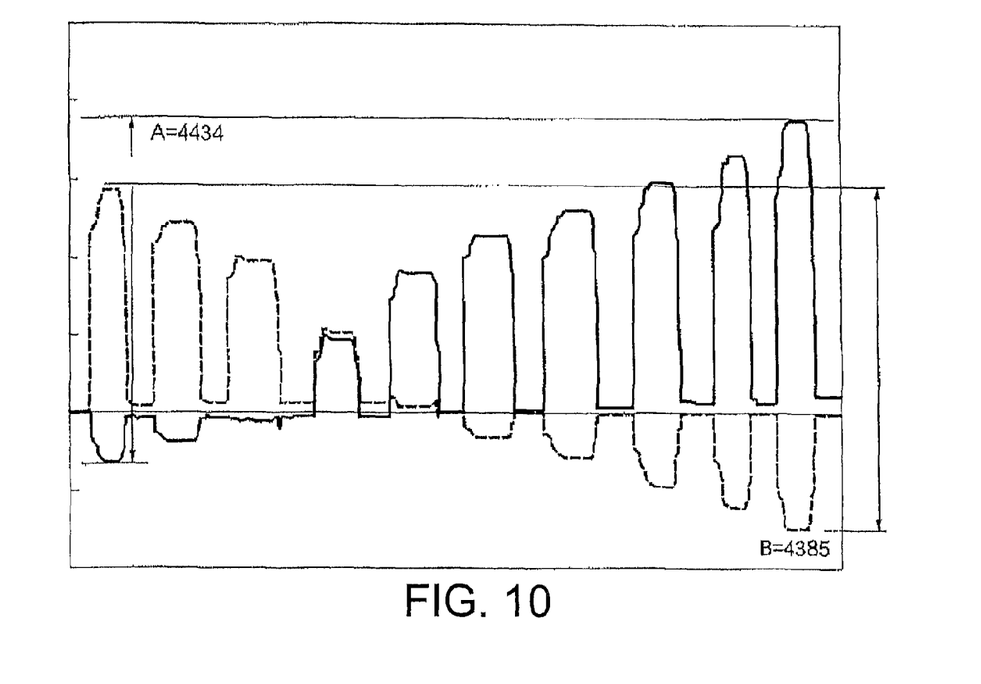
FIG. 10 is a graph showing one example of calibration of bonding errors of a strain gauge.

FIG. 10 shows one example of calibration of bonding errors. The Wheatstone bridge where the strain gauge in the first portion 481 involves is represented by A, and the Wheatstone bridge where the strain gauge in the second portion 482 involves is represented by B. In FIG. 10, the outputs of the respective Wheatstone bridges A, B are shown by broken lines and solid lines, respectively. The amplitude of the Wheatstone bridge A is "4434", while the amplitude of the other Wheatstone bridge B is "4385". Its ratio, i.e., B/(A+B) is 0.497. When the strain gauges involving in the respective Wheatstone bridges A, B are laterally symmetrically arranged, the value of P is "0.5". Therefore, the bonding errors can be calibrated serving the actual value of P as a calibration coefficient.

Mixed information of a load and moment (or torque) is output from the respective Wheatstone bridges A, B on the both sides (i.e., left and right). This information can be divided into a load Fz and a moment My by the addition processing and subtraction processing. In this respect, equations taking into consideration of the calibration coefficient P of the bonding errors are as follows.

Figure 11:
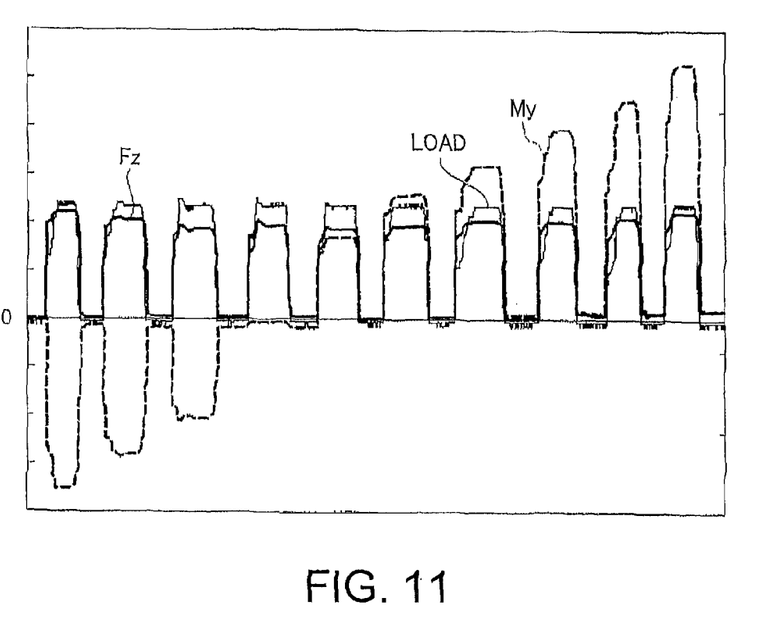
FIG. 11 is a graph showing an output example of the detection device obtained by calibration.

$Fz = P \times (\text{output of } A) + (1-P) \times (\text{output of } B)$ $My = P \times (\text{output of } A) - (1-P) \times (\text{output of } B)$ FIG. 11 shows each example of the load Fz and moment My which are calibrated taking the bonding errors into consideration. In FIG. 11, the load is shown by a thin solid line.

Figure 12:
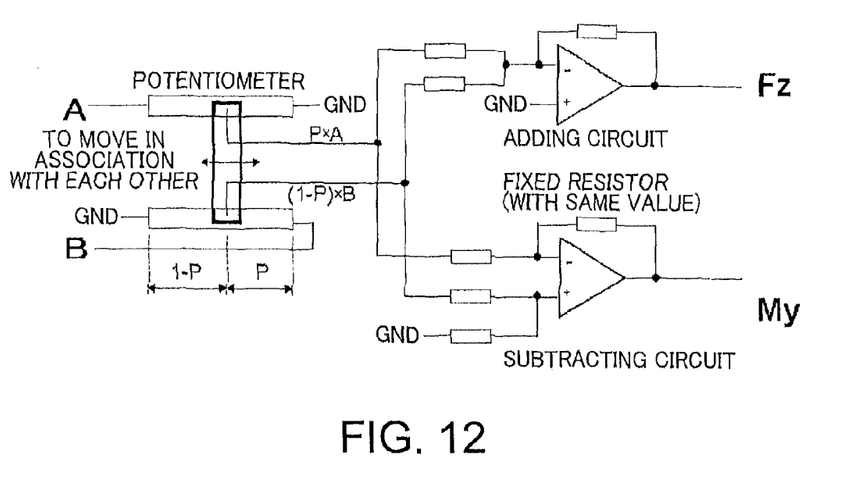
FIG. 12 is an electric circuit showing one example of a calculation circuit (or arithmetic circuitry) for calculating a load and a moment.

The calculation of the load Fz and moment My can be performed either by using a microcomputer for controlling the artificial leg 10 or an electrical circuit including an operational amplifier. FIG. 12 shows one example of the electrical circuit.

DESCRIPTION OF REFERENCE NUMERALS

10 . . . artificial leg (artificial limb)
12 . . . upper member
14 . . . lower member
16 . . . knee coupling
30 . . . detection device
40 . . . sensor block
421 . . . pyramid part
42 . . . base
422 . . . base body
44 . . . front side wall
46 . . . rear side wall
47 . . . space
48 . . . upper wall
480 . . . center portion
480a, 480b . . . attachment parts
481 . . . first portion
482 . . . second portion
50 . . . sensor bracket
70 . . . sensor fixing screw
80 . . . stopper means

The invention claimed is:

1. A detection device for detecting a load and moment comprising:
   a sensor block subject to an external force; and
   a strain gauge supported by said sensor block and adapted to detect a load and moment which are component of said external force,
   wherein
   (A) said sensor block includes:
   a base having an axis extending in a direction of said load;
   a front side wall raised from the base at a position offset from said axis of said base;
   a rear side wall raised from said base at a position offset from said axis of said base in the direction opposite said front side wall; and
   an upper wall for connecting an upper end of said front side wall and an upper end of said rear side wall,
   (B1) said upper wall includes:
   a center portion located at a center between said front side wall and said rear side wall; and constituting a part of said upper wall to which an object is attached, which utilizes the detection information of said load and moment;
   a first portion located between said center portion and said front side wall; and
   a second portion located between said center portion and said rear side wall,
   (B2) said center portion of said upper wall has a larger rigidity in comparison with said first and second portions, (C1) the strain gauge includes a first strain gauge disposed on an upper surface of said first portion of said upper wall, (C2) the strain gauge includes a second strain gauge disposed on an upper surface of the second portion of said upper wall, and (D) a load in a direction along said axis and a moment in a plane parallel to the offset direction of each of said front and rear side walls and perpendicular to an upper surface of said upper wall are detected by said first and second strain gauges, (E) a space is defined by said base, said upper wall, said front side wall and said rear side wall, and said upper wall is configured so that, when said object is attached to the center portion of said upper wall and the center portion of said upper wall is fixed, the external force applied to said base is transmitted to said upper wall through said front and rear side walls and the external force causes bending to said first and second portions.

2. The detection device according to claim 1, wherein attachment portions are each located on each end of said center portion in a direction perpendicular to the offset direction of said front and rear side walls, and said object, which utilizes the detection information of said load and moment, is fixed through said attachment portions.

3. The detection device according to claim 2, further comprising a ring-like fixing screw member for attaching and mutually fixing said sensor block and said object, and an amplifier for amplifying the detection output of said strain gauges is disposed in an internal circumferential space of said ring-like fixing screw.

4. The detection device according to claim 3, wherein at least a part of said sensor block is fit to a side of said object and a fit portion between at least the part of said sensor block and said side of said object is provided with a rotation prevention means including a non-circumferential plane.

5. The detection device according to claim 1, wherein said external force causes a bending onto said first and second portions of said upper wall, and the strain caused by said bending is detected by said first and second strain gauges.

6. The detection device according to claim 5, wherein the detection device is provided with stopper means for restricting a range of said bending, said stopper means includes a first stopper and a second stopper, said first stopper defining one side of the bending range and said second stopper defining the other side of the bending range.

7. The detection device according to claim 1, wherein a thickness of said center portion of said upper wall is larger than both a thickness of the first portion and a thickness of the second portion of said upper wall.

8. The detection device according to claim 1, wherein an upper surface position of the center portion of said upper wall is higher than an upper surface of any one of said first and second portions of said upper wall, and thus, a height of an upper surface of said attachment part is higher than a height position of any one of the upper surfaces of said first and second portions of said upper wall.

9. The detection device according to claim 1, wherein a lower surface position of said center portion of said upper wall is lower than a lower surface of any one of said first and second portions of said upper wall, and thus, a height of the lower surface of said attachment part is lower than a height position of any one of the lower surfaces of said first and second portions of said upper wall.

10. The detection device according to claim 1, wherein said first and second strain gauges are any one of a resistance strain gauge and a semiconductor strain gauge.

11. The detection device according to claim 1, wherein a thickness of said center portion of said upper wall is larger than a thickness of the first portion and a thickness of second portion of said upper wall, an upper surface position of the center portion of said upper wall is higher than an upper surface of any one of said first and second portions of said upper wall, and thus, a height of an upper surface of said attachment part is higher than a height position of any one of the upper surfaces of said first and second portions of said upper wall, and a lower surface position of said center portion of said upper wall is lower than a lower surface of any one of said first and second portions of said upper wall, and thus, a height of the lower surface of said attachment part is lower than a height position of any one of the lower surfaces of said first and second portions of said upper wall.

12. The detection device according to claim 1, wherein the front side wall and the center portion of said upper wall are away from each other by a distance equal to about half of the diameter of the upper wall; and the rear side wall and the center portion of said upper wall ware away from each other by a distance equal to about half of the diameter of the upper wall.

13. An artificial limb comprising an alignment block, wherein a detection device is built therein, said detection device comprising:

a sensor block subject to an external force; and a strain gauge supported by said sensor block and adapted to detect a load and moment which are component of said external force, wherein (A) said sensor block includes:

a base having an axis extending in a direction of said load;

a front side wall raised from the base at a position offset from said axis of said base;

a rear side wall raised from said base at a position offset from said axis of said base in the direction opposite said front side wall; and an upper wall for connecting an upper end of said front side wall and an upper end of said rear side wall, (B1) said upper wall includes:

a center portion located at a center between said front side wall and said rear side wall and constituting a part of said upper wall to which an object is attached, which utilizes the detection information of said load and moment;

a first portion located between said center portion and said front side wall; and a second portion located between said center portion and said rear side wall, (B2) said center portion of said upper wall has a larger rigidity in comparison with said first and second portions, (C1) the strain gauge includes a first strain gauge disposed on an upper surface of said first portion of said upper wall, (C2) the strain gauge includes a second strain gauge disposed on an upper surface of the second portion of said upper wall, and
(D) a load in a direction along said axis and a moment in a plane parallel to the offset direction of each of said front and rear side walls and perpendicular to an upper surface of said upper wall are detected by said first and second strain gauges,
(E) a space is defined by said base, said upper wall, said front side wall and said rear side wall, and
said upper wall is configured so that, when said object is attached to the center portion of said upper wall and the center portion of said upper wall is fixed, the external force applied to said based is transmitted to said upper wall through said front and rear side walls and the external force causes bending to said first and second portions and:
said sensor block is used as said alignment block.

* * * * *